(12) United States Patent
Cao et al.

(10) Patent No.: US 9,897,708 B2
(45) Date of Patent: Feb. 20, 2018

(54) POLAR EFFECT MODEL, SYSTEM, AND METHOD FOR PHOTON COUNTING DETECTOR IN MEDICAL IMAGING SYSTEMS INCLUDING COMPUTED TOMOGRAPHY

(71) Applicant: Toshiba Medical Systems Corporation, Otawara-shi (JP)

(72) Inventors: Chunguang Cao, Buffalo Grove, IL (US); Yu Zou, Naperville, IL (US); Xiaolan Wang, Buffalo Grove, IL (US); Miesher L. Rodrigues, Buffalo Grove, IL (US); Yuexing Zhang, Naperville, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 631 days.

(21) Appl. No.: 14/535,396

(22) Filed: Nov. 7, 2014

(65) Prior Publication Data

US 2016/0131773 A1 May 12, 2016

(51) Int. Cl.
*G01D 18/00* (2006.01)
*G01T 1/24* (2006.01)
(Continued)

(52) U.S. Cl.
CPC .............. *G01T 1/247* (2013.01); *A61B 6/032* (2013.01); *A61B 6/4241* (2013.01); *A61B 6/4266* (2013.01); *A61B 6/5205* (2013.01)

(58) Field of Classification Search
CPC ....... A61B 6/032; A61B 6/4241; A61B 6/482; A61B 6/4266; A61B 6/5205; A61B 6/4275; A61B 6/035; A61B 6/583; A61B 6/585; A61B 6/5258; A61B 6/5282; A61B 6/547; A61B 6/584; A61B 6/587; A61B 6/4441; A61B 6/467; A61B 6/488; A61B 6/037; A61B 6/4291; A61B 6/06; A61B 6/4208; A61B 6/5217; A61B 6/00; A61B 6/08;
(Continued)

(56) References Cited

U.S. PATENT DOCUMENTS

2004/0228451 A1* 11/2004 Wu .................. A61B 6/583
378/207
2006/0023832 A1* 2/2006 Edic ................ A61B 6/032
378/7

OTHER PUBLICATIONS

Jian Zhou, et al., "Fast and efficient fully 3D PET image reconstruction using sparse system matrix factorization with GPU acceleration" Phys Med Biol., vol. 56, No. 20, Oct. 21, 2011, 29 Pages.

* cited by examiner

*Primary Examiner* — Irakli Kiknadze
(74) *Attorney, Agent, or Firm* — Oblon, McClelland, Maier & Neustadt, L.L.P.

(57) ABSTRACT

An apparatus and a method are provided for calculating an output spectrum of a photon-counting detector based on an incident spectrum. The apparatus includes processing circuitry to determine a plane extending from a top face of the photon-counting detector that includes regions that all possible incident rays will transverse; divide the determined plane into subregions; calculate a detector response function for each of the subregions; determine an overall detector response function by summing the calculated detector response function for each of the subregions and normalizing the summation by an area of the determined plane; and calculate the output spectrum based on the overall detector response function and the incident spectrum.

19 Claims, 12 Drawing Sheets

(51) Int. Cl.
*A61B 6/00* (2006.01)
*A61B 6/03* (2006.01)
(58) Field of Classification Search
CPC .. A61B 2017/00725; A61B 2090/3762; A61B 2503/40; A61B 5/0013
USPC .................................. 378/4, 15, 19, 62, 207
See application file for complete search history.

POLAR EFFECT MODEL, SYSTEM, AND METHOD FOR PHOTON COUNTING DETECTOR IN MEDICAL IMAGING SYSTEMS INCLUDING COMPUTED TOMOGRAPHY

FIELD

The exemplary embodiments described herein relate to photon-counting detector systems.

BACKGROUND

Computed tomography (CT) systems and methods are widely used, particularly for medical imaging and diagnosis. CT systems generally create images of one or more sectional slices through a subject's body. A radiation source, such as an X-ray tube, irradiates the body from one side. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

These conventional detectors are called energy-integrating detectors for acquiring energy integration X-ray data. Recently, photon-counting detectors are configured to acquire the spectral nature of the X-ray source rather than the energy integration nature in acquiring data. To obtain the spectral nature of the transmitted X-ray data, the photon-counting detectors split the X-ray beam into its component energies or spectrum bins and count a number of photons in each of the bins. The use of the spectral nature of the X-ray source in CT is often referred to as spectral CT. Since spectral CT involves the detection of transmitted X-rays at two or more energy levels, spectral CT generally includes dual-energy CT by definition.

Semiconductor-based photon-counting detectors used in spectral CT can detect incident photons and measure photon energy for every event. However, due to the interaction depth and ballistic deficit, the measured photon energy cannot be related to incident photon energy uniquely. At high flux, pulse pileup may cause count lose too. Therefore, as recognized by the present inventor, a detector response function for semiconductor-based photon-counting detectors (e.g., CZT or CdTe) is required to describe the count rate nonlinearity and energy response.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION

In a hybrid photon-counting CT design, a ring of sparsely distributed photon-counting detectors are used to acquire spectral information in a fourth-generation CT geometry, while energy-integrating detectors acquire data using a third-generation geometry. The fourth-generation design can overcome challenges facing photon-counting detector technology, while the third-generation data can be used to maintain the spatial resolution and noise characteristics of the reconstruction.

In one embodiment, there is provided an apparatus for calculating an output spectrum of a photon-counting detector based on an incident spectrum, the apparatus comprising: processing circuitry configured to (1) determine a plane extending from a top face of the photon-counting detector that includes regions that all possible incident rays will transverse; (2) divide the determined plane into subregions; (3) calculate a detector response function for each of the subregions; (4) determine an overall detector response function by summing the calculated detector response function for each of the subregions and normalizing the summation by an area of the determined plane; and (5) calculate the output spectrum based on the overall detector response function and the incident spectrum.

In another embodiment, there is provided a method for calculating an output spectrum of a photon-counting detector based on an incident spectrum, the method comprising: (1) determining a plane extending from a top face of the photon-counting detector that includes subregions that all possible incident rays will transverse; (2) dividing the determined plane into subregions; (3) calculating a detector response function for each of the subregions; (3) determining an overall detector response function by summing the calculated detector response function for each of the subregions and normalizing the summation by an area of the determined plane; and (4) calculating the output spectrum based on the overall detector response function and the incident spectrum.

In another embodiment, there is provided a non-transitory computer-readable medium storing executable instructions, which when executed by a computer processor, cause the computer processor to execute a method comprising: (1) determining a plane extending from a top face of the photon-counting detector that includes subregions that all possible incident rays will transverse; (2) dividing the determined plane into subregions; (3) calculating a detector response function for each of the subregions; (4) determining an overall detector response function by summing the calculated detector response function for each of the subregions and normalizing the summation by an area of the determined plane; and (5) calculating the output spectrum based on the overall detector response function and the incident spectrum.

Figure 1:
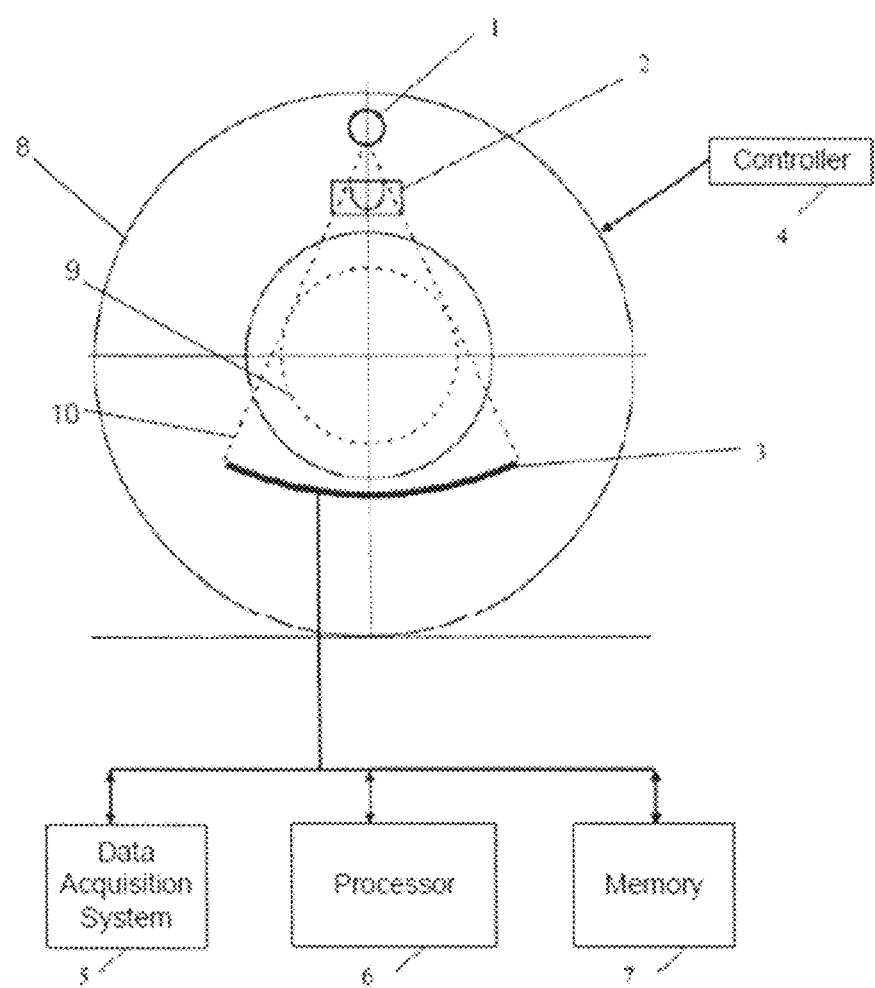
FIGS. 1 and 2 illustrate exemplary CT scanner systems.

FIG. 1 illustrates a simplified schematic structure of a CT apparatus that can include a detector array to detect photons. Aspects of this disclosure are not restricted to a CT apparatus as the medical imaging system. In particular, the structures and procedures described herein can be applied to other medical imaging systems, and the descriptions provided herein specifically relating to a CT apparatus and the detection of photons should be considered as exemplary.

Figure 2:
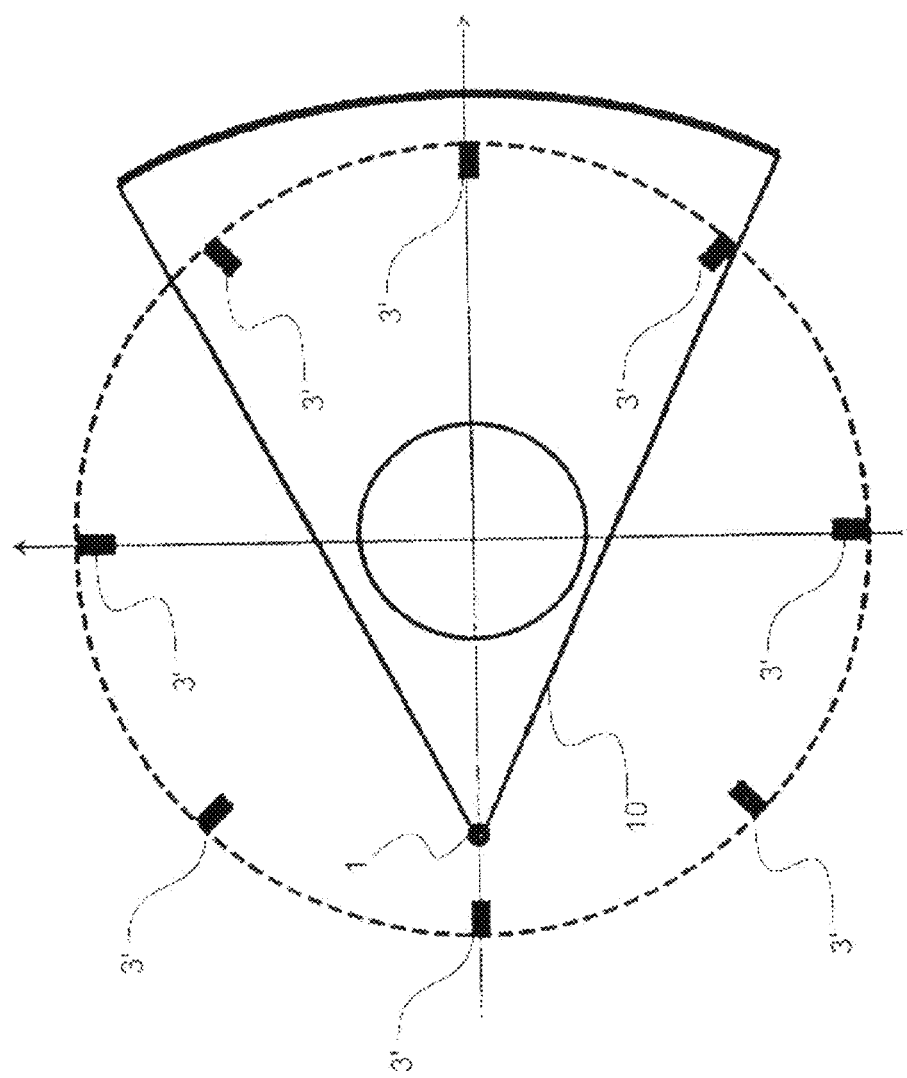

A detector array, a photon detector and/or a photon detector array may be referred to herein merely as a detector. The CT apparatus illustrated in FIG. 1 includes an X-ray tube 1, filters and collimators 2, and a third-generation detector 3. The CT apparatus can also include sparse fixed energy-discriminating (e.g., photon-counting) detectors 3', which can be arranged at a different radius from that of the third-generation detector, as shown in FIG. 2. The CT apparatus also includes additional mechanical and electrical components such as a gantry motor and a controller 4 to control the rotation of the gantry, control the X-ray source, and control a patient bed. The CT apparatus also includes a data acquisition system 5 and a processor 6. The processor 6 is configured to generate CT images based on the projection (view) data acquired by the data acquisition system. For example, the processor 6 includes a reconstruction processor to reconstruct spectral CT images. The processor is programmed to perform methods and execute algorithms in accordance with the processes, algorithms, equations, and relationships described herein. The processor and data acquisition system can make use of a memory 7, which is configured to store, e.g., data obtained from the detector, detector pile-up models, and reconstructed images.

The X-ray tube 1, filters and collimators 2, detector 3, and controller 4 can be provided in a frame 8 that includes a bore. The frame 8 has a general cylindrical or donut shape. In the view shown in FIG. 1, a longitudinal axis of the bore of the frame 8 is in the center of the bore and extends into and out of the page. An interior of the bore, identified as area 9, is a target area for imaging. An object to be scanned, such as a patient, is placed in the target area with, e.g., a patient table. The object can then be irradiated by the X-ray tube 1 with a fan or cone of radiation 10, which generally, substantially or effectively cross-sects the object with respect to the longitudinal axis. The processor 6 is programmed to determine photon counts of captured incident X-ray photons. The data acquisition system 5, the processor 6, and the memory 7 can be implemented as a single machine or computer, or as separate machines or computers that are coupled together or distributed via a network or other data communication system. The controller 4 can also be coupled via the network or other data communication system, and can be implemented by a separate machine or computer, or as part of another machine or computer of the system.

In FIG. 1, the detector 3 is a rotational detector array that rotates with the X-ray tube 1 with respect to the longitudinal axis. Although not shown in FIG. 1, a stationary detector array can also be included, thus providing a rotating detector array and a stationary array, together, in the frame 8. Other detectors can be implemented.

Many clinical applications can benefit from spectral CT technology, including improvement in material differentiation and beam-hardening correction.

Semiconductor-based photon-counting detector can detect incident photons and measure photon energy for every event, and is thus a promising candidate for spectral CT, capable of providing better spectral information compared with conventional spectral CT technology (e.g., dual-source, kVp-switching, etc.).

However, photon-counting detectors have reduced tolerance against high X-ray flux. A photon-counting detector has to be able to count every individual photon separately in order to determine its energy content. When photon interaction occurs too rapidly, the electrical signal caused by individual events can merge. As a consequence, only a single event with an increased energy is counted, an effect called "pileup".

Furthermore, in a fourth-generation CT scanner, the detectors are on a stationary gantry, and the X-ray source rotates. The detector receives X-rays from different incident angles as the source rotates. The detector response varies with the X-ray incident angle, which is referred to as the polar effect. The polar effect needs to be considered and integrated into the detector response model for the hybrid photon-counting CT scanner. The polar effect needs to be considered and integrated into the detector response model for the sparse fourth-generation photon-counting detector geometry.

Figure 3A:
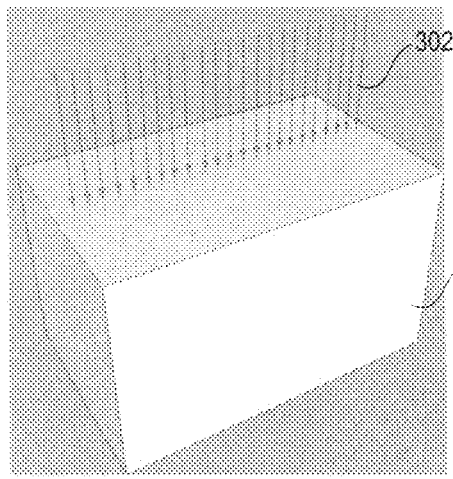
FIG. 3A illustrates a schematic of incident rays of photons perpendicular to a detector element's top surface.
Figure 3B:
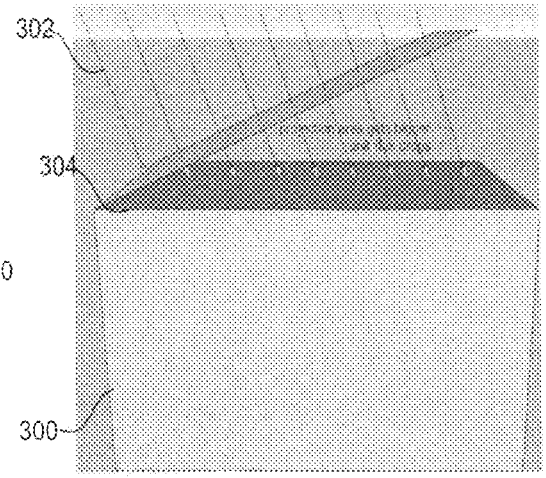
FIG. 3B illustrates a schematic of the incident rays of the photons not perpendicular to the detector element's top surface.

The polar effect usually happens for a non-normal entrance of incident photons, results in ambiguity in determining the response of the detector, and degrades the overall spatial resolution. When the incident photons 302 are not perpendicular to the top face 304 of the detector 300, as shown in FIG. 3B, or when the photons enter through the side face 306, as shown in FIG. 3C, the geometrical efficiency of the detector is different from the case of normal incidence through the top face 304 shown in FIG. 3A.

Figure 3C:
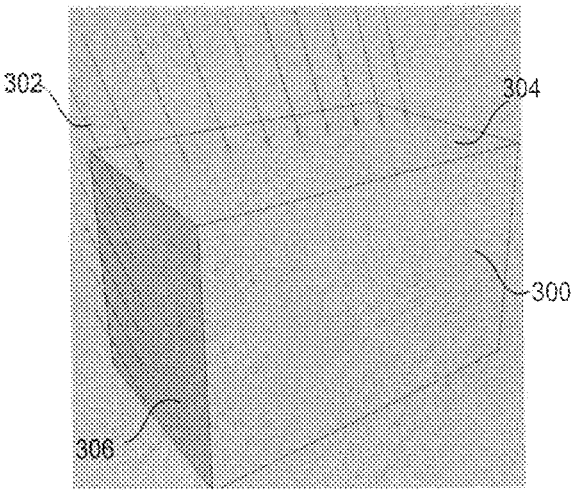
FIG. 3C illustrates a schematic of the incident rays of the photons at the top and side surface of the detector elements.

Moreover, photons entering the detector element from different locations, e.g., the top face 304 and the side face 306, travel different distances through the detector, as shown in FIG. 3C, which causes photons in different rays to have different energy responses, and different detection efficiencies, etc.

Furthermore, when pileup exists, i.e., at high flux, the quasi-coincident photons can enter the detector from multiple combinations of the top and the side faces. Pulse pileup occurring at high X-ray fluxes can severely degrade the energy resolution provided by a photon-counting detector, which is a problem in spectroscopic CT when performing quantitative material-discrimination tasks.

To best model the polar effect and the pileup effect in photon-counting detectors, a polar-effect modelling method is described herein.

Figure 4:
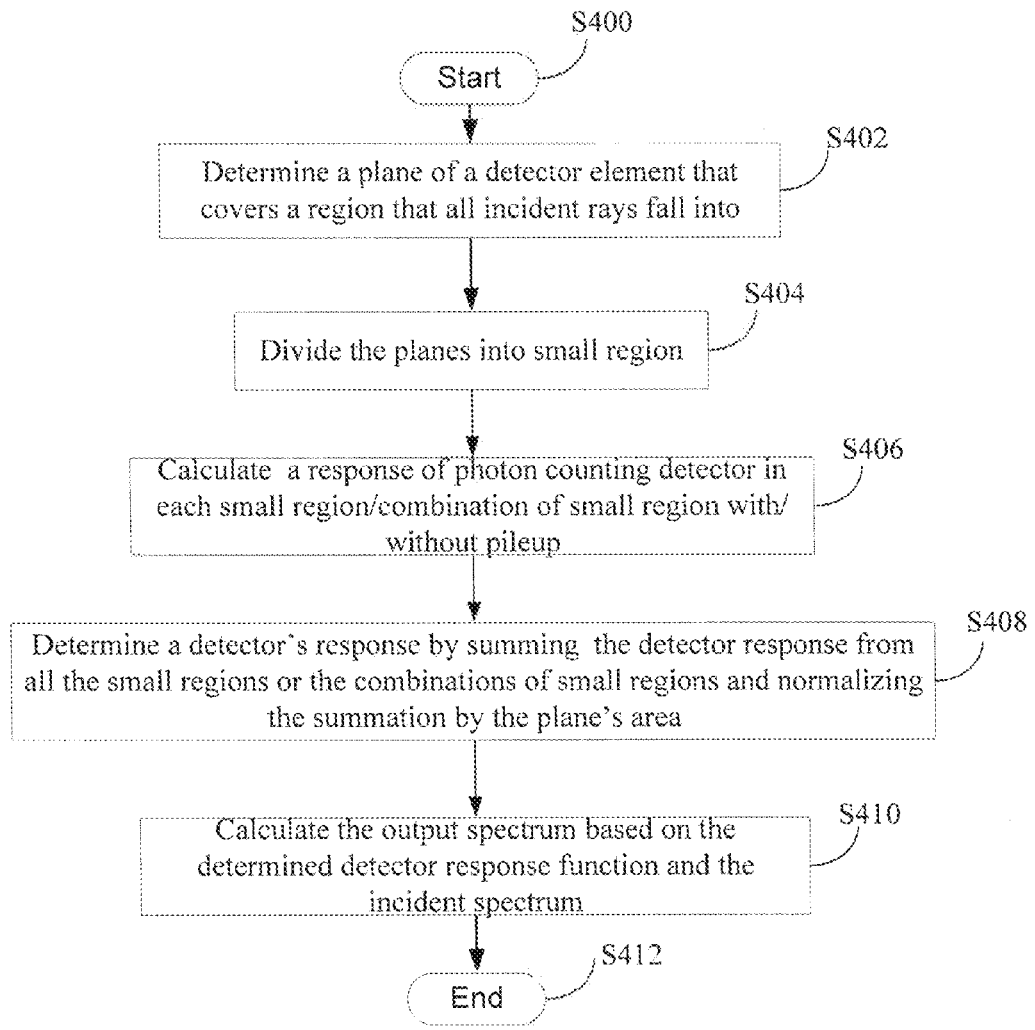
FIG. 4 illustrates a general method of modeling polar effects in a detector element.

Referring to FIG. 4, a flowchart 400 is shown describing a method performed by processing circuitry for reducing the polar effect and the pileup effect in a photon-counting detector using a normalization method.

In step 402, the processing circuitry determines a plane of a detector element that covers a region that all incident rays fall into.

In step 404, the processing circuitry divides the plane into small regions. The length and width of the small regions are determined based on the geometry of the detector element and the precision requirement of the polar effect model. For example, a suitable area of the small region can be 0.1 mm by 0.1 mm, which can satisfy the precision requirement of the polar effect model. A region with an area that is smaller than 0.1 mm by 0.1 mm cannot increase the precision of the polar effect model to a large degree. Therefore, for a detector's top face with an area of 1 mm by 2 mm, the top face can be divided into 10×20 subregions, for example, and each of the subregions has an area of 0.1 mm by 0.1 mm.

In step 406, the processing circuitry calculates a response of the photon-counting detector based on a model in each small region with and without pile-up.

In step 408, the processing circuitry determines the overall detector response by summing the detector responses from all of the small regions or a combination of the small regions, and normalizing the summation by the area of the plane.

In step 410, the processing circuitry calculates the output spectrum based on the determined detector response and the incident spectrum.

In one embodiment, after step 408, the overall detector response function is stored in the memory 7 and, in step 410, the processing circuitry is further configured to read out the overall detector response function from the memory 7 and calculate the output spectrum based on the incident spectrum and the overall detector response function read out from the memory 7.

Figure 5A:
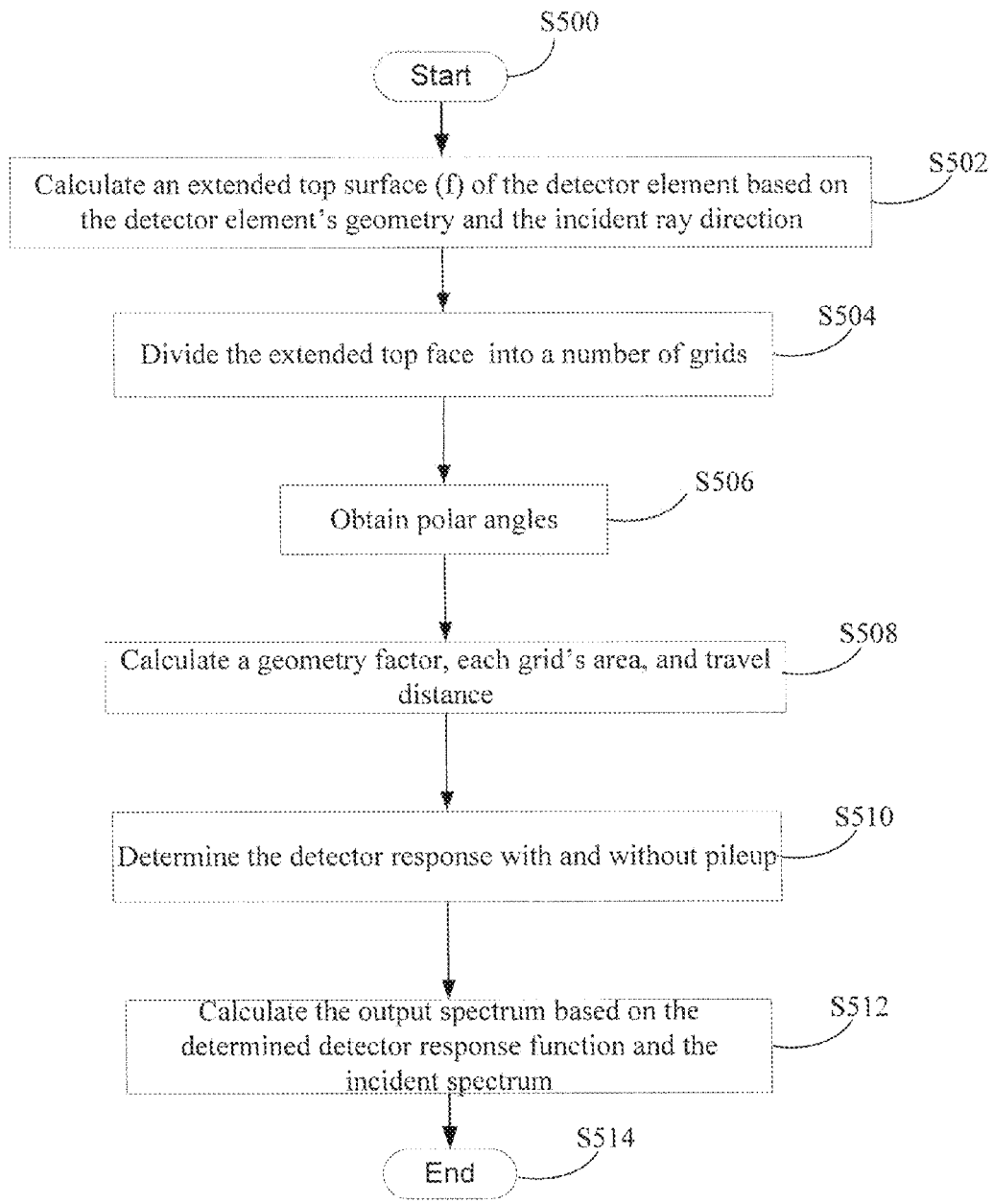
FIG. 5A illustrates an embodiment of modeling polar effects in a detector element.

Referring to FIG. 5A, a flowchart 500 describes a specific embodiment of the method described in flowchart 400.

Figure 5B:
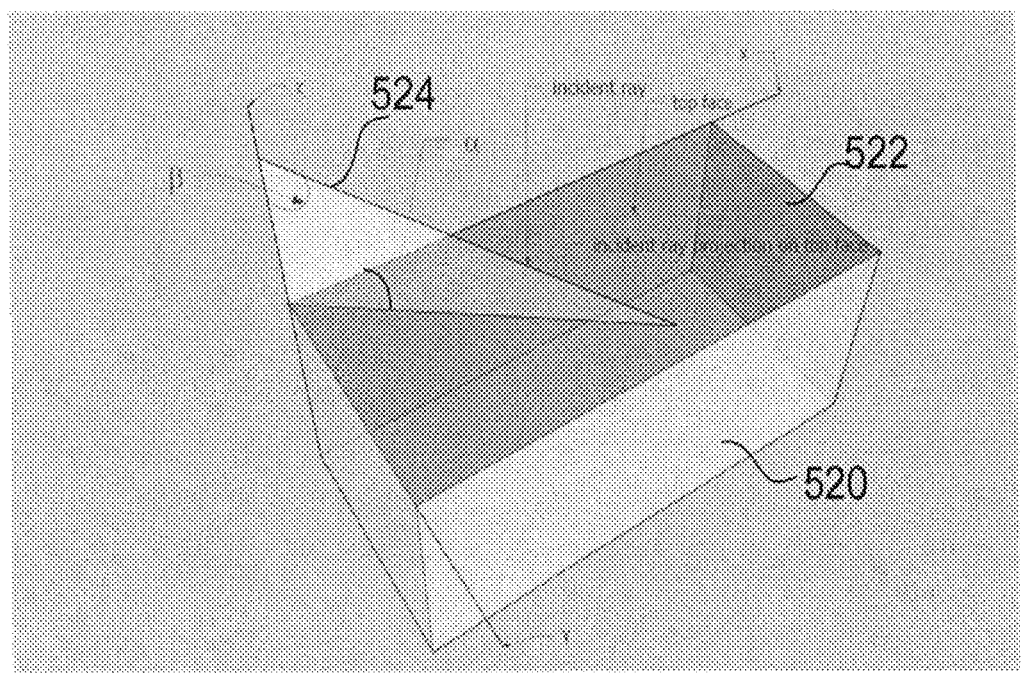
FIG. 5B, FIG. 5C, and FIG. 5D illustrate, according to this embodiment, angles to define the incident ray direction, schematics of an extended top face of the detector element, and divided small subregions at the extended top face.

In step 502, an angle $\alpha$ and an angle $\beta$ of an incident ray are determined by the CT system. As shown in FIG. 5B, the angle $\alpha$ is the angle between the X-axis and the projection of an incident ray 524 on the face 522, and the angle $\beta$ is the angle between the direction of the incident ray 524 and the normal of face 522. Angles $\alpha$ and $\beta$ are used to define the direction of the incident ray 524.

Figure 5C:
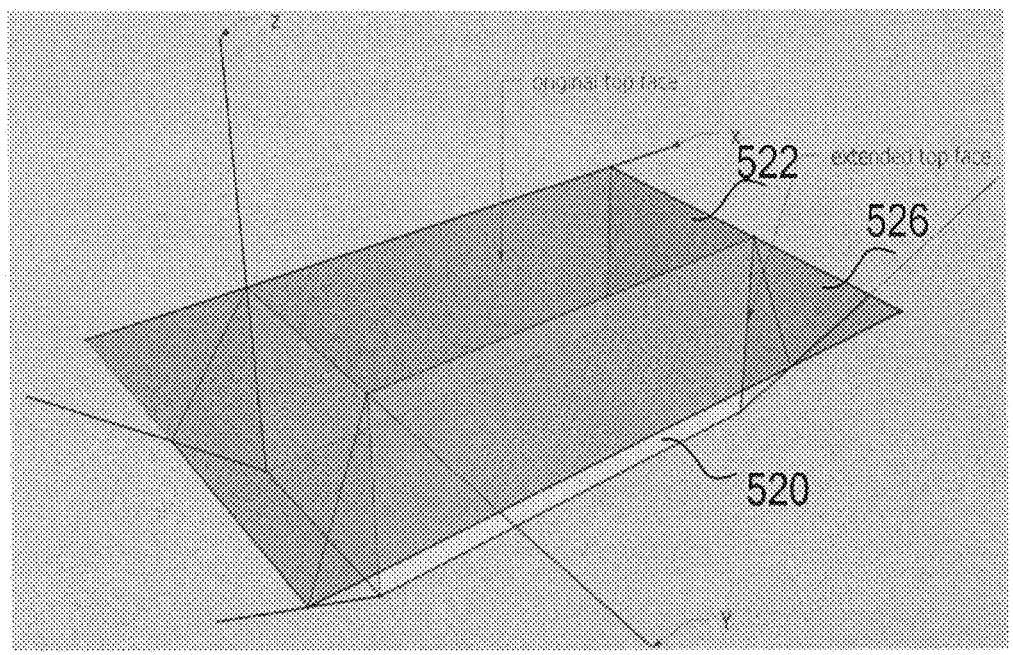

In step 504, the processing circuitry calculates an extended top surface 524 of the detector 520 based on the detector's geometry and the incident ray direction, as shown in FIG. 5C.

A 3D detector element 520 shown in FIG. 5C may be extended to form a larger top surface 526 including extra area from its side surfaces. Four vertices at the bottom face of the detector can be defined as: $(0, 0, D_h)$, $(0, D_w, D_h)$, $(D_l, 0, D_h)$, and $(D_l, D_w, D_h)$, where $D_l$, $D_w$, and $D_h$ are a length, a width, and a height of the detector 520, respectively. Each of the four vertices at the bottom face is projected in a direction $I_{inv}$ that is opposite to the direction of the incident ray to generate an intersection point with the plane that includes the top face 522. The eight points, which include the four intersections points and the four original vertices at the top face of the detector, are defined as $I_i=(x_i,y_i,0)$, where i=0 . . . 7. The four vertices of the extended top face can be calculated as $(\min_x,\min_y,0),(\min_x,\max_y,0),(\max_x,\min_y,0)$, and $(\max_x,\max_y,0)$, respectively, wherein
$\min_x=\text{minimum}(x_i),\min_y=\text{minimum}(y_i)$,
$\max_x=\text{maximum}(x_i),\max_x=\text{maximum}(y_i)$.

Figure 5D:
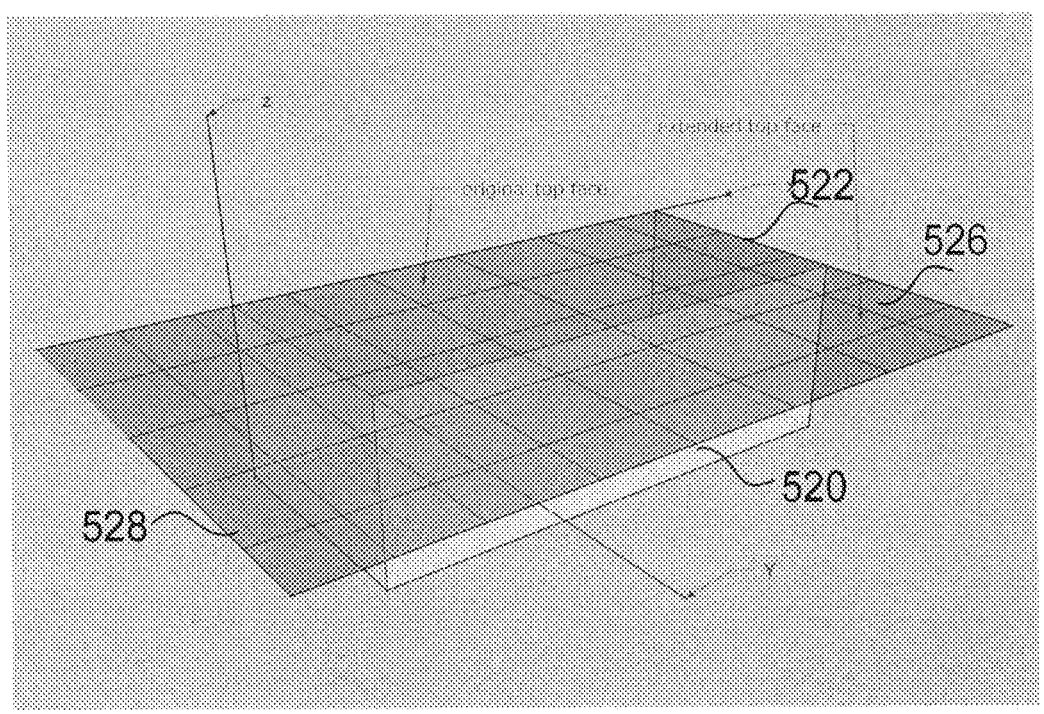

In step 506, the processing circuitry divides the extended top face 526 into a number of subregions 528, $g_{ij}$, wherein i and j are the subregion indices in the X and Y dimensions and i=0 . . . m, j=0 . . . n, as shown in FIG. 5D, wherein m and n are integers. For a first-order pile-up (two photons pileup), the processing circuitry further divides the extended top face 526 into a number of subregions 528 that a second photon is located, $g_{kl}$, wherein k and l are the subregion indices in the X and Y dimensions and k=0 . . . e, l=0 . . . h, wherein e and h are integers. Similarly, for s order pileup, the processing circuitry continues to divide the extended top face 526 into a number of subregions 528 that each of the s photons is located. The exact number of subregions 528 depends on factors such as the detector's geometric dimensions, the polar angle, etc. The subregions 528 may have the same or different areas. The method to divide the top surface is similar to step 404.

In step 508, the processing circuitry calculates a geometric factor: $G=\cos(\beta)$, each subregion's area that the first photon is located $a_{ij}$ and distance, $L_{ij}$, wherein $L_{ij}$ is a distance that the photon travels inside the detector element for each subregion, $g_{ij}$, and each subregion's area that the second photon is located $a_{kl}$ and distance, $L_{kl}$, wherein $L_{kl}$ is a distance that the photon travels inside the detector element for each subregion, $g_{kl}$.

In step 510, the processing circuitry determines the detector response without pileup and with pileup. The detector's response without pileup is calculated according to equation (1):

$$R^0(E, E_0) = e^{-n_0 \tau_d} \frac{\sum_{i=0}^{m}\sum_{j=0}^{n} \int_{L_{ij}} \chi_0 P_{ij}^0 dz}{A} \quad (1)$$

wherein $$P_{ij}^0 = a_{ij} \times G \times e^{-\mu(E_0)\frac{z}{\sin(\beta)}} \times \frac{\mu(E_0)}{\sin(\beta)}, \mu(E_0)$$

is the detector's attenuation, $n_0$ is the incident flux, z is the photon's coordinate in the z direction, $\tau_d$ is the dead time, $\chi_0$ (=1) is detection probability without pileup, $E_0$ is the incident photon energy, E is the detected energy of the incident photon, and A is the area of the extended top surface 526.

The detector's response to a first-order pileup (two photons pileup) $R^1$ is calculated by summing up all the responses produced by any combinations of the two photons from two subregions 528 according to equation (2):

$$R^1(E, E_0, E_1) = n_0 e^{-n_0 \tau_d} \frac{\sum_{i=0}^{m}\sum_{j=0}^{n}\sum_{k=0}^{m}\sum_{l=0}^{n} \int\int_{L_{kl}} \int_{L_{ij}} \chi_1 P_{ij,kl}^1 dz_0 dz_1 dt_1}{A^2} \quad (2)$$

wherein $$P_{ij,kl}^1 = a_{ij} \times G \times a_{kl} \times G \times e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)},$$

$$\chi_1( = 0.5)$$

is the detection probability of first-order pileup, $z_0$ and $z_1$ are the first and second photons' z coordinates, respectively, $E_0$ and $E_1$ are the first and second incident photon's energy, respectively, $t_1$ is the time interval between the arrival of the first and the second incident photons, $\mu(E_0)$ is the detector's attenuation at incident energy $E_0$, $\mu(E_1)$ is the detector attenuation at incident energy $E_1$, $a_{ij}$ is the area of subregion $g_{ij}$, and $a_{kl}$ is the area of subregion $g_{kl}$.

Similarly, the detector's response to a second-order pileup (three photons pileup) $R^2$ is calculated by summing up all of the responses produced by any combination of the three photons from three subregions 528. Higher-order pileup cases can be processed is a similar way. Different numbers of subregions 528 may be used for different-order pileup cases to save computation time. Also, an approximation method can be used for pileup of order two and above to save computation time.

In step 512, the processing circuitry calculates an output spectrum based on the incident spectrum. An overall equation to calculate the output spectrum based on incident spectrum:

$$S_m(E) = \int dE_0 R^0(E,E_0) S_{in}(E_0) + \iint dE_0 dE_1 R^1(E,E_0,E_1) S_{in}(E_0) S_{in}(E_1) \quad (3)$$

wherein $S_m(E)$ is the modeled output spectrum, and $S_{in}(E)$ is the incident spectrum.

Once a photon interacts in the detector element, regardless of the incident polar angle, the detected and incident energies are related by equation (4):

$$E = v_p(t_{TOF}^0; z_0, E_0) \quad (4)$$

wherein E is the detected energy of the incident photon, $E_0$ is the incident energy, $z_0$ is the point where an X-ray photon converts to electron-hole pairs, $t_{TOF}^0$ is the time that the generated electrons drifts from the interaction point $z_0$ to the anode of the detector. In other words, the relationship between the detected energy and the incident energy is only determined by the charge collection property of the detector, e.g., the depth of interaction and the weighting potential, and is independent of the polar angle.

Figure 6A:
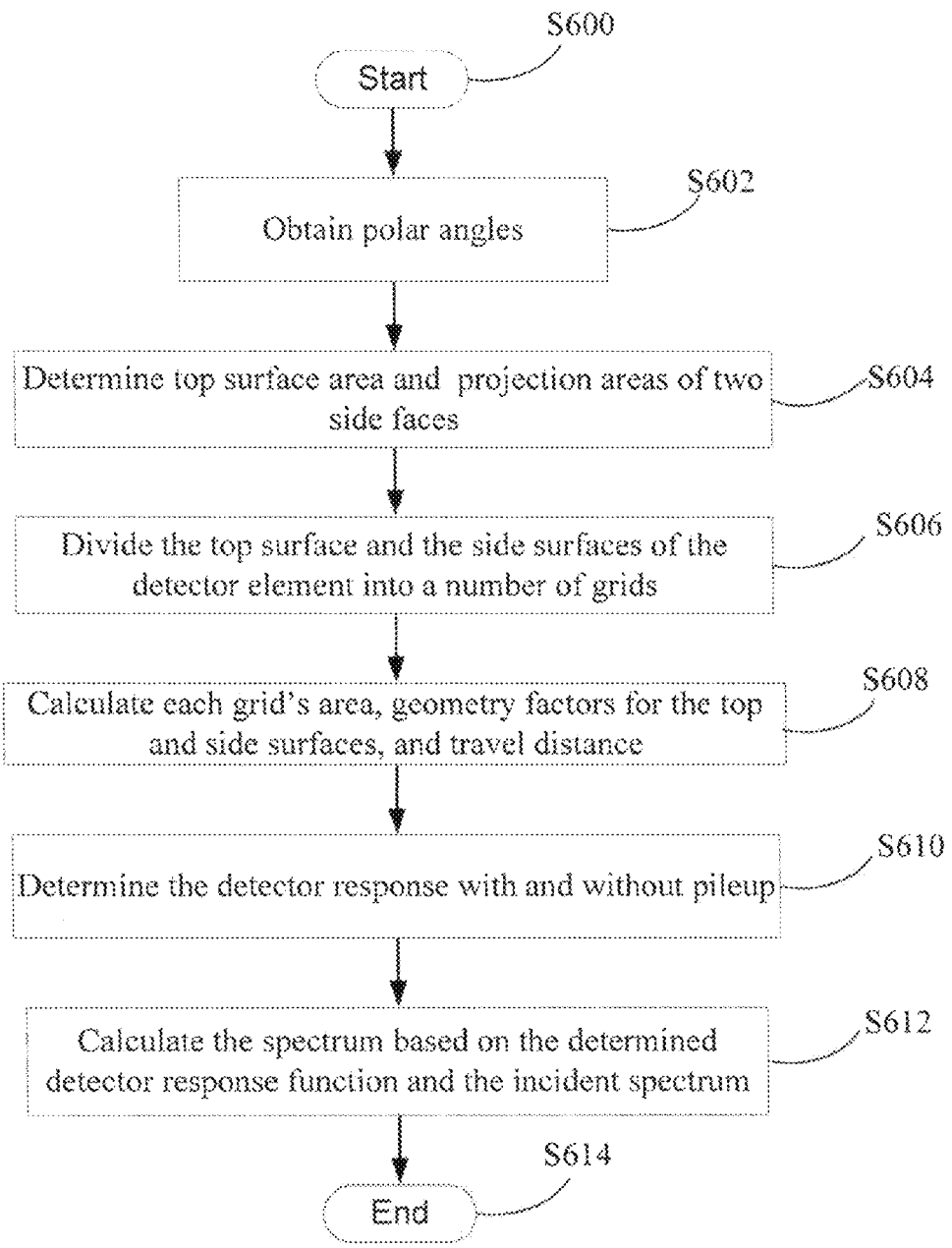
FIG. 6A illustrates another embodiment of modeling polar effects in a detector element.

Referring to FIG. 6A, a flowchart 600 is shown describing another specific embodiment of the method described in flowchart 400.

In step 602, an angle α and an angle β of an incident ray are determined by the CT system. The angle α is the angle between the X-axis and the projection of the incident ray on the original top surface, and the angle β is the angle between the incident ray's direction and the normal of original top surface. Angles α and β are used to define the direction of the incident ray.

In step 604, the processing circuitry determines the area of the top face b (622) and the projection area of side faces c (624) and d (626) of the detector element 620 that is exposed to the incident rays. The area of top face b (622) is $A_b$. The projection area of the side faces is along the incident ray direction on the plane f where the top face 620 is located, and the projection areas of at most two side faces are calculated according to equations (5) and (6):

$$A_c^p = A_c \times \tan(\beta)\cos(\alpha) \quad (5)$$

$$A_d^p = A_d \times \tan(\beta)\sin(\alpha) \quad (6)$$

wherein $A_c$ is the area of face c (624), $A_d$ is the area of face d (626), the angle α is the angle between the X-axis and the projection of the incident ray on the plane f, and the angle β is the angle between the incident ray's direction and the normal of the plane f.

Figure 6B:
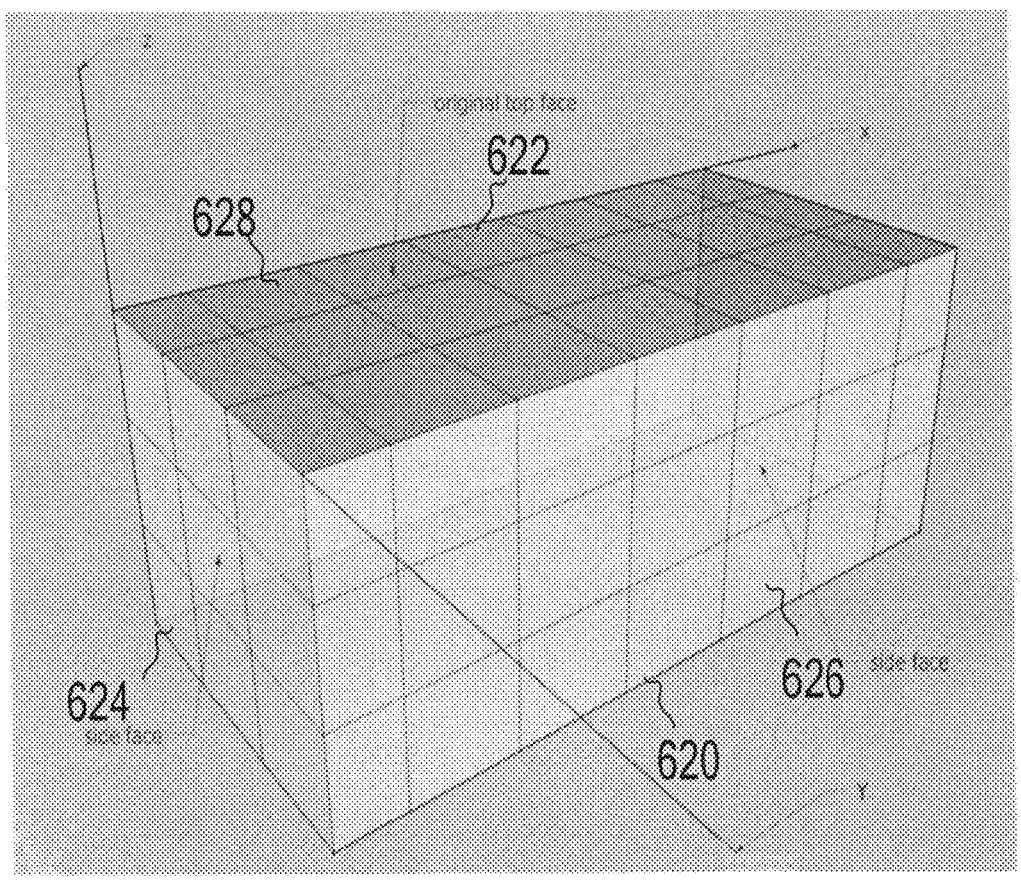
FIG. 6B illustrates, according to this embodiment, divided small subregions at the top and the side faces.

In step 606, the processing circuitry divides the top face b (622), and the side faces c (624) and d (626) of the detector 620 into a number of subregions (628), $g_{i_b j_b}$, $g_{i_c j_c}$, and $g_{i_d j_d}$ respectively, wherein, $i_b$ and $j_b$ are the subregion indices of a first photon in the X and Y dimensions of the face b, where $i_b = 0 \ldots m$, $j_b = 0 \ldots n$, $i_c$ and $j_c$ are the subregion indices of the first photon in the X and Y dimensions of the face c, where $i_c = 0 \ldots p$, $j_c = 0 \ldots q$, $i_d$ and $j_d$ are the subregion indices of the first photon in the X and Y dimensions of the face d, and $j_d = 0 \ldots r$, $j_d = 0 \ldots t$, as shown in FIG. 6B. m, n, p, q, r, and t are integers. The exact number of subregions used depends on factors such as the detector's geometric dimensions, the polar angle, etc. For a first-order pile-up (two photons pileup), the processing circuitry further divides the top face b, and the side faces c and d of the detector into a number of subregions 628 that a second photon is located, $g_{k_b l_b}$, $g_{k_c l_c}$, and $g_{k_d l_d}$ respectively, wherein $k_b$ and $l_b$ are the subregion indices of the second photon in the X and Y dimensions of the face b, where $k_b = 0 \ldots e$, $l_b = 0 \ldots h$, $k_c$ and $l_c$ are the subregion indices of the second photon in the X and Y dimensions of the face c, where $k_c = 0 \ldots o$, $l_c = 0 \ldots u$, $k_d$ and $l_d$ are the subregion indices of the second photon in the X and Y dimensions of the face d, and $k_d = 0 \ldots v$, $l_d = 0 \ldots w$, where e, h, o, u, v, and w are integers. Similarly, for s order pileup, the processing circuitry continues to divide the extended top face f into a number of subregions that each of the s photons is located.

In step 608, the processing circuitry calculates each subregion's area that the first photon is located $a_{i_b j_b}$, $a_{i_c j_c}$ and $a_{i_d j_d}$, respectively, each subregion's area that the second photon is located $a_{k_b l_b}$, $a_{k_c l_c}$ and $a_{k_d l_d}$, respectively, geometric factors for the top surface b, the side surface c, and the side surface d, and distances $L_{i_b j_b}$, $L_{i_c j_c}$, $L_{i_d j_d}$, $L_{k_b l_b}$, $L_{k_c l_c}$, and $L_{k_d l_d}$, wherein $a_{i_b j_b}$ is each subregion's area that the first photon is located on the surface b, $a_{i_c j_c}$ is each subregion's area that the first photon is located on the surface c, $a_{i_d j_d}$ is each subregion's area that the first photon is located on the surface d, $a_{k_b l_b}$ is each subregion's area that the second photon is located on the surface b, $a_{k_c l_c}$ is each subregion's area that the second photon is located on the surface c, $a_{k_d l_d}$ is each subregion's area that the second photon is located on the surface d, $L_{i_b j_b}$ is a distance that the first photon travels inside the detector on the face b for each subregion, $L_{i_c j_c}$ is a distance that the first photon travels inside the detector on the face c for each subregion, $L_{i_d j_d}$ is a distance that the first photon travels inside the detector on the face d for each subregion, $L_{k_b l_b}$ is a distance that the second photon travels inside the detector on the face b for each subregion, $L_{k_c l_c}$ is a distance that the second photon travels inside the detector on the face c for each subregion, and $L_{k_d l_d}$ is a distance that the second photon travels inside the detector on the face d for each subregion.

The processing circuitry calculates geometric factors for the top surface b and the side surfaces c and d according to equations (7)-(9):

$$G_b = \cos(\beta) \quad (7)$$

$$G_c = \sin(\beta)\cos(\alpha) \quad (8)$$

$$G_d = \sin(\beta)\sin(\alpha) \quad (9)$$

wherein the angle α is the angle between the X-axis and the projection direction of an incident ray on the plane f, and the angle β is the angle between the incident ray's direction and the normal of the plane f as shown in FIG. 5B.

In step 610, the processing circuitry calculates the detector response without pileup and with pileup. The detector's response without pileup is the combination of the responses from the top and side faces, and is calculated according to equation (10):

$$R^0(E, E_0) = \frac{R_b^0 + R_c^0 + R_d^0}{A_b + A_c^p + A_d^p} \quad (10)$$

wherein $$R_b^0(E, E_0) = e^{-n_0 \tau_d} \sum_{i_b=0}^{m_b} \sum_{j_b=0}^{n_b} \int_{L_{i_b j_b}} X_0 P_{i_b j_b}^0 dz,$$

$$R_c^0(E, E_0) = e^{-n_0 \tau_d} \sum_{i_c=0}^{m_c} \sum_{j_c=0}^{n_c} \int_{L_{i_c j_c}} X_0 P_{i_c j_c}^0 dz,$$

-continued $$R_d^0(E, E_0) = e^{-n_0\tau_d} \sum_{i_d=0}^{m_d} \sum_{j_d=0}^{n_d} \int_{L_{i_d j_d}} \chi_0 P_{i_d j_d}^0 dz,$$

$$P_{i_c j_c}^0 = a_{i_c j_c} \times G_c \times e^{-\mu(E_0)\frac{z}{\sin(\beta)}} \times \frac{\mu(E_0)}{\sin(\beta)},$$

$$P_{i_b j_b}^0 = a_{i_b j_b} \times G_b \times e^{-\mu(E_0)\frac{z}{\sin(\beta)}} \times \frac{\mu(E_0)}{\sin(\beta)},$$

$$P_{i_d j_d}^0 = a_{i_d j_d} \times G_d \times e^{-\mu(E_0)\frac{z}{\sin(\beta)}} \times \frac{\mu(E_0)}{\sin(\beta)}.$$

Here $\chi_0(=1)$ is the detection probability without pileup, $\mu(E_0)$ is the detector's attenuation, $G_b$ is a geometric factor for the top surface b, $G_c$ is a geometry factor of the side surface c, $G_d$ is a geometric factor for the side surface d, $A_b$ is the area of the top surface b, $A_c^p$ is the projection area of the side surface c, $A_d^p$ is the projection area of the side surface d, $R_b^0$ is the detector response without pileup for the top surface b, $R_c^0$ is the detector response without pileup for the side surface c, and $R_d^0$ is the detector response without pileup for the side surface d.

The detector's response to a first-order pileup (two photons pileup) is the combination of the responses from the top and side faces, and is calculated according to equation (11):

$$R^1(E, E_0, E_1) = \frac{R_{bb}^1 + R_{cc}^1 + R_{dd}^1 + R_{bc}^1 + R_{bd}^1 + R_{cd}^1}{(A_b + A_c^p + A_d^p) \times (A_b + A_c^p + A_d^p)} \quad (11)$$

wherein $$R_{bb}^1(E, E_0, E_1) =$$
$$n_0 e^{-n_0\tau_d} \sum_{i_b=0}^{m_b} \sum_{j_b=0}^{n_b} \sum_{k_b=0}^{m_b} \sum_{l_b=0}^{n_b} \int \int_{L_{k_b l_b}} \int_{L_{i_b j_b}} \chi_1 P_{i_b j_b, k_b l_b}^1 dz_0 dz_1 dt_1,$$

$$R_{cc}^1(E, E_0, E_1) =$$
$$n_0 e^{-n_0\tau_d} \sum_{i_c=0}^{m_c} \sum_{j_c=0}^{n_c} \sum_{k_b=0}^{m_c} \sum_{l_c=0}^{n_c} \int \int_{L_{k_c l_c}} \int_{L_{i_c j_c}} \chi_1 P_{i_c j_c, k_c l_c}^1 dz_0 dz_1 dt_1,$$

$$R_{dd}^1(E, E_0, E_1) =$$
$$n_0 e^{-n_0\tau_d} \sum_{i_d=0}^{m_d} \sum_{j_d=0}^{n_d} \sum_{k_d=0}^{m_d} \sum_{l_d=0}^{n_d} \int \int_{L_{k_d l_d}} \int_{L_{i_d j_d}} \chi_1 P_{i_d j_d, k_d l_d}^1 dz_0 dz_1 dt_1,$$

$$R_{bc}^1(E, E_0, E_1) =$$
$$n_0 e^{-n_0\tau_d} \sum_{i_b=0}^{m_b} \sum_{j_b=0}^{n_b} \sum_{k_c=0}^{m_c} \sum_{l_c=0}^{n_c} \int \int_{L_{k_b l_b}} \int_{L_{i_c j_c}} \chi_1 P_{i_b j_b, k_c l_c}^1 dz_0 dz_1 dt_1,$$

$$R_{bd}^1(E, E_0, E_1) =$$
$$n_0 e^{-n_0\tau_d} \sum_{i_b=0}^{m_b} \sum_{j_b=0}^{n_b} \sum_{k_d=0}^{m_d} \sum_{l_d=0}^{n_d} \int \int_{L_{k_b l_b}} \int_{L_{i_d j_d}} \chi_1 P_{i_b j_b, k_d l_d}^1 dz_0 dz_1 dt_1,$$

$$R_{cd}^1(E, E_0, E_1) =$$
$$n_0 e^{-n_0\tau_d} \sum_{i_c=0}^{m_c} \sum_{j_c=0}^{n_c} \sum_{k_d=0}^{m_d} \sum_{l_d=0}^{n_d} \int \int_{L_{k_c l_c}} \int_{L_{i_d j_d}} \chi_1 P_{i_c j_c, k_d l_d}^1 dz_0 dz_1 dt_1,$$

$$P_{i_b j_b, k_b l_b}^1 = a_{i_b j_b} \times G_b \times a_{k_b l_b} \times G_b \times$$
$$e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)},$$

$$P_{i_c j_c, k_c l_c}^1 = a_{i_c j_c} \times G_c \times a_{k_c l_c} \times G_c \times$$
$$e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)},$$

$$P_{i_d j_d, k_d l_d}^1 = a_{i_d j_d} \times G_d \times a_{k_d l_d} \times G_d \times$$
$$e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)},$$

$$P_{i_b j_b, k_c l_c}^1 = a_{i_b j_b} \times G_b \times a_{k_c l_c} \times G_c \times$$
$$e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)},$$

$$P_{i_b j_b, k_d l_d}^1 = a_{i_b j_b} \times G_b \times a_{k_d l_d} \times G_d \times$$
$$e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)},$$

$$P_{i_c j_c, k_d l_d}^1 = a_{i_c j_c} \times G_c \times a_{k_d l_d} \times G_d \times$$
$$e^{-\mu(E_0)\frac{z_0}{\sin(\beta)} - \mu(E_1)\frac{z_1}{\sin(\beta)}} \times \frac{\mu(E_0)}{\sin(\beta)} \times \frac{\mu(E_1)}{\sin(\beta)}.$$

Here $R_{bb}^1$ is a detector response when the two photons that pile up are both from face the b, $R_{cc}^1$ is a detector response when the two photons that pile up are both from the face c, $R_{dd}^1$ is a detector response when the two photons that pile up are both from the face d, $R_{bc}^1$ is a detector response when the two photons the pile up are from the face b and the face c, $R_{bd}^1$ is a detector response when the two photons that pile up are from the face b and the face d, $R_{cd}^1$ is a detector response when the two photons that pile up are from the face c and the face d, $A_b$ is the area of the top surface b, $A_c^p$ is the projection area of the side surface c, $A_d^p$ is the projection area of the side surface d, $\chi_1(=0.5)$ is the detection probability of first-order pileup, $G_b$ is a geometric factor for the top surface b, $G_c$ is a geometry factor of the side surface c, $G_d$ is a geometric factor for the side surface d, $z_0$ and $z_1$ are the first and second photon's coordinates in the z direction, respectively, $E_0$ and $E_1$ are the first and second incident photon's energy, respectively, $t_1$ is the time interval between an arrival of the first and the second incident photons, $A_b$ is the area of the top surface b, $\mu(E_0)$ is the detector attenuation at incident energy $E_0$, $\mu(E_1)$ is the detector attenuation at incident energy $E_1$, $A_c^p$ is the projection area of the side surface c, $A_d^p$ is the projection area of the side surface d, $a_{i_b j_b}$ is the area of each subregion that the first photon is located on the surface b, $a_{i_c j_c}$ is the area of each subregion that the first photon is located on the surface c, $a_{i_d j_d}$ is the area of each subregion that the first photon is located on the surface d, $a_{k_b k_b}$ is the area of each subregion that the second photon is located on the surface b, $a_{k_c k_c}$ is the area of each subregion that the second photon is located on the surface c, and $a_{k_d k_d}$ is the area of each subregion that the second photon is located on the surface d.

Higher-order pileup cases can be processed is a similar way. An approximation method can be used in pileup of order two and above to save computation time.

In step 612, the processing circuitry calculates an output spectrum based on the incident spectrum and the calculated detector responses $R^0$, $R^1$, $R^2$, $R^3$, etc. An overall equation to calculate the output spectrum based on incident spectrum according to equation (3).

In an alternative embodiment, a different number of subregions 628 can be used for $R^0$, $R^1$, $R^2$, $R^3$, etc. to save computation time. Further, in another embodiment, a different number of subregions 628 can be used for different detector element faces or in different regions of the extended top face of the detector element to save computation time and improve accuracy.

The disclosed embodiments perform realistic polar effect integrations over all the incident surfaces in the photon-counting detector response models that model the polar effect with and without pileup effect. With the extended top face, all the incident rays can be treated in a unified manner, regardless of the entrance faces.

Figure 7A:
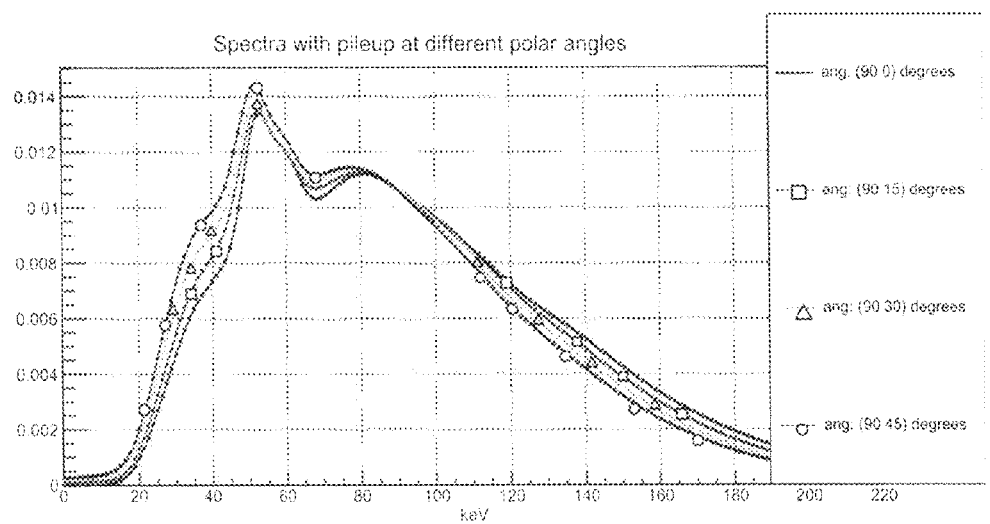
FIG. 7A shows a graph illustrating exemplary modeled spectra with different polar angles.

FIG. 7A shows a graph illustrating exemplary modeled spectra for varying polar angles α and β. Modeled spectra with polar angles (α, β) as (90,0), (90,15), (90,30), and (90,45), respectively, are shown.

Figure 7B:
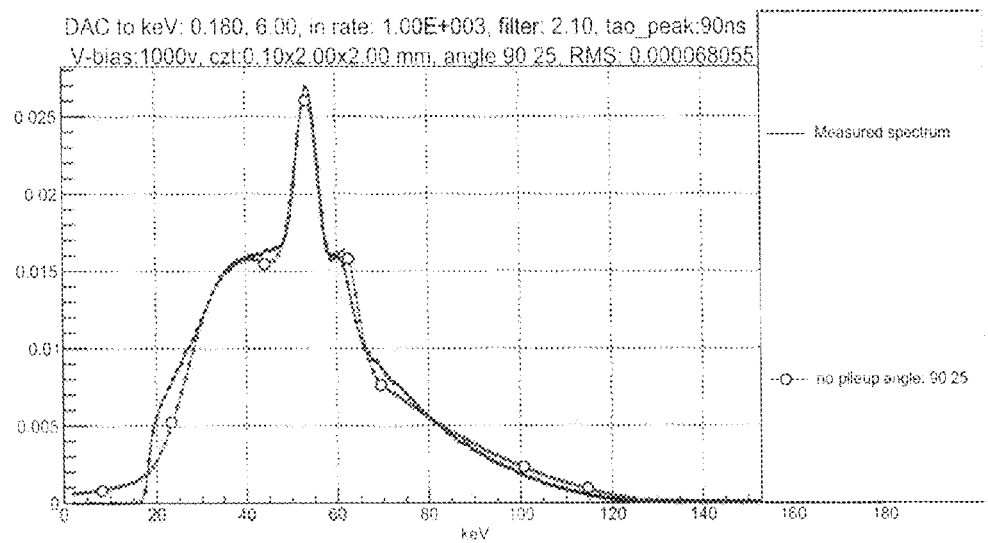
FIG. 7B shows a graph illustrating a comparison of a modeled spectrum with a measured spectrum at polar angle (90, 25) without pileup effects.

FIG. 7B shows a graph illustrating a comparison of a modeled spectrum with a measured spectrum at polar angle (90, 25) with no pileup effects. It is evident that the model can realistic represent the polar effects.

Figure 8:
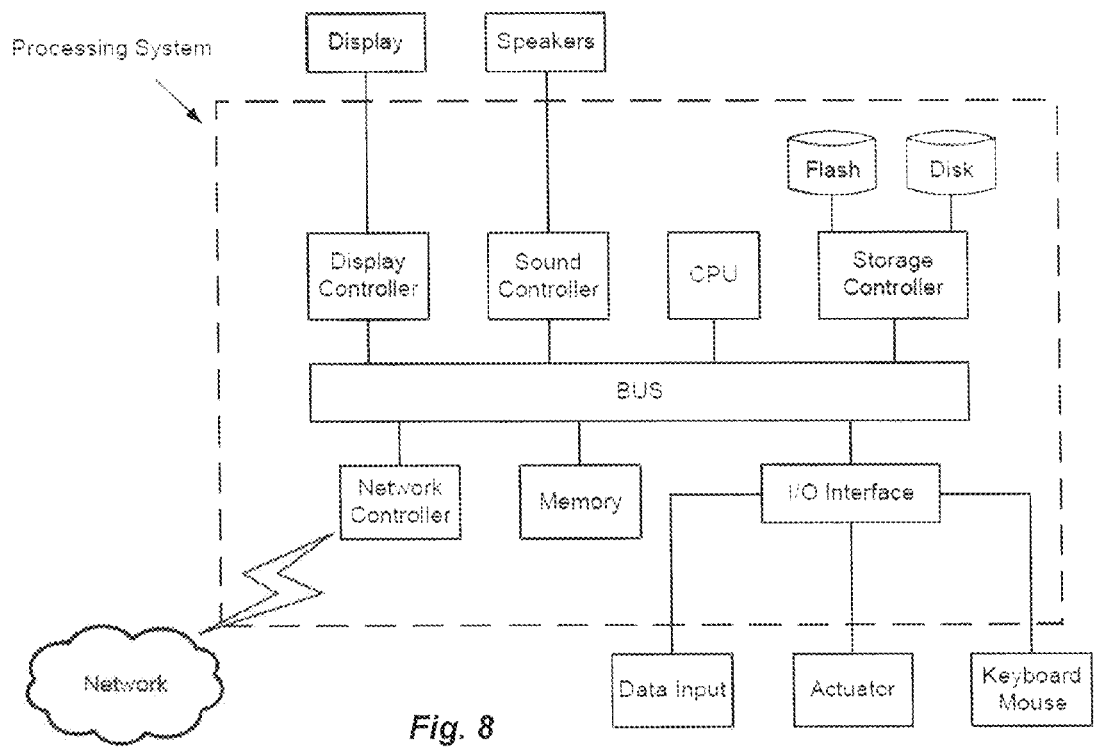
FIG. 8 shows a schematic diagram of an exemplary processing system.

An exemplary processing system is illustrated in FIG. 8, which is an exemplary implementation of the processor 6 of FIG. 1. The processor 6 can be a hardware device, e.g., a CPU that has been specifically configured to execute one or more computer programs that cause the CPU to perform the functions illustrated in the flowcharts of FIGS. 4, 5A, and 6A. In particular, this exemplary processing system can be implemented using one or more microprocessors or the equivalent, such as a central processing unit (CPU) and/or at least one application-specific processor ASP (not shown). A microprocessor is a circuit or circuitry that utilizes a computer readable storage medium, such as a memory circuit (e.g., ROM, EPROM, EEPROM, flash memory, static memory, DRAM, SDRAM, and their equivalents), configured to control the microprocessor to perform and/or control the processes and systems of this disclosure, and configured to execute the algorithms described herein. Other storage mediums can be controlled via a controller, such as a disk controller, which can controls a hard disk drive or optical disk drive.

The microprocessor or aspects thereof, in alternate implementations, can include or exclusively include a logic device for augmenting or fully implementing aspects of this disclosure. Such a logic device includes, but is not limited to, an application-specific integrated circuit (ASIC), a field programmable gate array (FPGA), a generic-array of logic (GAL), and their equivalents. The microprocessor can be a separate device or a single processing mechanism. Further, this disclosure can benefit from parallel processing capabilities of a multi-cored CPU and a graphics processing unit (GPU) to achieve improved computational efficiency. One or more processors in a multi-processing arrangement may also be employed to execute sequences of instructions contained in memory. Alternatively, hard-wired circuitry may be used in place of or in combination with software instructions. Thus, the exemplary implementations discussed herein are not limited to any specific combination of hardware circuitry and software.

In another aspect, results of processing in accordance with this disclosure can be displayed via a display controller to a monitor. The display controller preferably includes at least one graphic processing unit, which can be provided by a plurality of graphics processing cores, for improved computational efficiency. Additionally, an I/O (input/output) interface is provided for inputting signals and/or data from microphones, speakers, cameras, a mouse, a keyboard, a touch-based display or pad interface, etc., which can be connected to the I/O interface as a peripheral. For example, a keyboard or a pointing device for controlling parameters of the various processes or algorithms of this disclosure can be connected to the I/O interface to provide additional functionality and configuration options, or control display characteristics. Moreover, the monitor can be provided with a touch-sensitive interface for providing a command/instruction interface.

The above-noted components can be coupled to a network, such as the Internet or a local intranet, via a network interface for the transmission or reception of data, including controllable parameters. A central bus is provided to connect the above hardware components together and provides at least one path for digital communication there between.

The data acquisition system 5, the processor 6, and the memory 7 of FIG. 1 can be implemented utilizing one or more processing systems in accordance with the exemplary implementation shown in FIG. 8. In particular, one or more circuits or computer hardware units coinciding with one or more of the devices illustrated in FIG. 1 can provide for the functions of the data acquisition system 5, the processor 6, and the memory 7 (collectively or separately). The functional processing described herein can also be implemented in specialized circuitry or one or more specialized circuits including circuits to perform the described processing. Such circuits can be a part of a computer processing system or a discrete device that is interconnected to other systems. A processor in accordance with this disclosure can also be programmed to or configured to execute the functional processing described herein by computer code elements.

Further, the processing systems, in one implementation, can be connected to each other by a network or other data communication connection. One or more of the processing systems can be connected to corresponding actuators to actuate and control movement of the gantry, the X-ray source, and/or the patient bed.

Suitable software can be tangibly stored on a computer readable medium of a processing system, including the memory and storage devices. Other examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read. The software may include, but is not limited to, device drivers, operating systems, development tools, applications software, and/or a graphical user interface.

Computer code elements on the above-noted medium may be any interpretable or executable code mechanism, including but not limited to scripts, interpretable programs, dynamic link libraries (DLLs), Java classes and complete executable programs. Moreover, parts of the processing of aspects of this disclosure may be distributed for better performance, reliability and/or cost.

The data input portion of the processing system accepts input signals from a detector or an array of detectors by, e.g., respective wired connections. A plurality of ASICs or other data processing components can be provided as forming the Data Input portion, or as providing input(s) to the data input portion. The ASICs can receive signals from, respectively, discrete detector arrays or segments (discrete portions) thereof. When an output signal from a detector is an analog signal, a filter circuit can be provided, together with an analog-to-digital converter for data recording and processing uses. Filtering can also be provided by digital filtering, without a discrete filter circuit for an analog signal. Alternatively, when the detector outputs a digital signal, digital filtering and/or data processing can be performed directly from the output of the detector.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. An apparatus for calculating an output spectrum of a photon-counting detector based on an incident spectrum, the apparatus comprising:
processing circuitry configured to
determine a plane extending from a top face of the photon-counting detector that includes regions that all possible incident rays will transverse;
divide the determined plane into subregions;
calculate a detector response function for each of the subregions;
determine an overall detector response function by summing the calculated detector response function for each of the subregions and normalizing the summation by an area of the determined plane; and
calculate the output spectrum based on the overall detector response function and the incident spectrum,
wherein the processing circuitry is further configured to divide the determined plane into subregions in which a first photon is located and subregions in which a second photon is located, each subregion in which the first photon is located being designated by $g_{ij}$ and each subregion in which the second photon is located being designated by $g_{kl}$, wherein i and j are indices of the subregions in which the first photon is located in X and Y dimensions, and i=0 . . . m, j=0 . . . n, k and l are indices of the subregions in which the second photon is located in the X and Y dimensions, and k=0 . . . e, l=0 . . . h, and m, n, e and h are integers.

2. The apparatus of claim 1, further comprising:
a radiation source configured to emit X-rays and to rotate around an object to be scanned;
a plurality of detectors arranged around the object and configured to detect the emitted X-rays; and
circuitry configured to reconstruct an image based on the calculated output spectrum, wherein the detectors include the photon-counting detector.

3. The apparatus of claim 1, wherein the processing circuitry is further configured to determine an angle α and an angle β, wherein the angle α is an angle between the X-axis and a projection direction of an incident ray on a top face, and the angle β is an angle between the projection direction of the incident ray and a normal of the top face.

4. The apparatus of claim 3, wherein the processing circuitry is further configured to calculate a geometric factor G=cos(β), an area $a_{ij}$ of each subregion in which the first photon is located, an area $a_{kl}$ of each subregion in which the second photon is located, a distance $L_{ij}$, wherein $L_{ij}$ is a distance that a photon travels inside the detector for the subregion $g_{ij}$, and a distance $L_{kl}$, wherein $L_{kl}$ is a distance that a photon travels inside the subregion $g_{kl}$.

5. The apparatus of claim 4, wherein the processing circuitry is further configured to determine a detector response function with no pileup based on an attenuation of the detector, an incident flux, a coordinate of an incident photon in a z direction, a dead time, a detection probability without pileup, an incident photon energy, a detected energy of the incident photon, and an area of the top plane extended.

6. The apparatus of claim 5, wherein the processing circuitry is further configured to determine a detector response function with first-order pileup based on a detection probability of first-order pileup, the calculated geometry factor, coordinates of first and second incident photons in the z direction, an energy of the first and second incident photons, a time interval between an arrival of the first and the second incident photons, and an detector attenuation at the incident energy of the first incident photon.

7. The apparatus of claim 6, wherein the processing circuitry is further configured to determine the overall detector response function for s-order pileup of s photons by summing up the calculated detector response functions for each of the subregions produced by any combination of s photons from s subregions, and weighting the summed detector response functions by an area of the top face, wherein s is an integer >1.

8. The apparatus of claim 7, wherein the processing circuitry is further configured to divide the determined plane into a different number of subregions for different order pileup to reduce computation time.

9. The apparatus of claim 1, wherein the processing circuitry is further configured to determine one or two side surfaces that are exposed to the incident rays and projected on the top face of the detector.

10. The apparatus of claim 9, wherein the processing circuitry is further configured to divide a top surface b and side surfaces c and d into a number of subregions in which a first photon is located, $g_{i_b j_b}$, $g_{i_c j_c}$, and $g_{i_d j_d}$, respectively, and into a number of subregions in which a second photon is located, $g_{k_b l_b}$, $g_{k_c l_c}$, and $g_{k_d l_d}$, wherein $i_b$ and $j_b$ are indices of the subregions in which the first photon is located in X and Y dimensions of the top face b, wherein $i_b$=0 . . . m, $j_b$=0 . . . n, $i_c$ and $j_c$ are indices of the subregions in which the first photon is located in the X and Y dimensions of the side surface c, wherein $i_c$=0 . . . p, $j_c$=0 . . . q, $i_d$ and $j_d$ are indices of the subregions in which the first photon is located in the X and Y dimensions of the side surface d, wherein $i_d$=0 . . . r, $j_d$=0 . . . t, $k_b$ and $l_b$ are indices of the subregions in which the second photon is located in the X and Y dimensions of the top face b, wherein $k_b$=0 . . . e, $l_b$=0 . . . h, $k_c$ and $k_c$ are indices of the subregions in which the second photon is located in the X and Y dimensions of the side surface c, wherein $k_c$=0 . . . o, $l_c$=0 . . . u, $k_d$ and $l_d$ are indices of the subregions in which the second photon is located in the X and Y dimensions of the side surface d, wherein $k_d$=0 . . . v, $l_d$=0 . . . w, and m, n, p, q, t, e, h, o, u, v and w are integers.

11. The apparatus of claim 10, wherein the processing circuitry is further configured to calculate an area of each subregion in which the first photon is located as $a_{i_b j_b}$, $a_{i_c j_c}$ and $a_{i_d j_d}$, an area of each subregion in which the second photon is located as $a_{k_b l_b}$, $a_{k_c l_c}$ and $a_{k_d l_d}$, the calculated geometric factors for the top surface b, the side surface c, and the side surface d, and $L_{i_b j_b}$, $L_{i_c j_c}$, $L_{i_d j_d}$, $L_{k_b l_b}$, $L_{k_c l_c}$, and $L_{k_d l_d}$, wherein $L_{i_b j_b}$ is a distance that the first photon travels inside the detector at the face b for each subregion $g_{i_b j_b}$, $L_{i_c j_c}$ is a distance that the first photon travels inside the detector at the face c for each subregion $g_{i_c j_c}$, $L_{i_d j_d}$ is a distance that the second photon travels inside the detector at the face d for each subregion $g_{i_d j_d}$, $L_{k_b l_b}$ is a distance that the second photon travels inside the detector at the face b for each subregion $g_{k_b l_b}$, $L_{k_c l_c}$ is a distance that the second photon travels inside the detector at the face c for each subregion $g_{k_c l_c}$, and $L_{k_d l_d}$ is a distance that the second photon travels inside the detector at the face d for each subregion $g_{k_d l_d}$.

12. The apparatus of claim 11, wherein the processing circuitry is further configured to determine the geometric factors for the top face b and the side surfaces c and d based on an angle between the X-axis and a projection direction of the incident ray on the top face, and an angle between the projection direction of the incident ray and a normal of the top face.

13. The apparatus of claim 12, wherein the processing circuitry is further configured to calculate projection areas of the side surfaces c and d on the determined plane based on an area of the side surface c, an area of the side surface d, the projection area of the side surface c, and the projection area of the side surface d.

14. The apparatus of claim 13, wherein the processing circuitry is further configured to determine a detector response function with no pileup based on a detection probability without pileup, an attenuation of the detector, a coordinate of an incident photon in a z direction, an incident photon energy, a detected energy of incident photons, a detector response without pileup for the top surface b, a detector response without pileup for the side surface c, and a detector response without pileup for the side surface d.

15. The apparatus of claim 14, wherein the processing circuitry is further configured to determine a response function with first-order pileup based on a detector response when two photons that pile up are both from a top surface b, a detector response when the two photons that pile up are both from the a side surface face c, a detector response when the two photons that pile up are both from a side surface face d, a detector response when the two photons that pile up are from the top surface b and the side surface c, a detector response when the two photons that pile up are from the top face b and the side surface face d, a detector response when the two photons that pile up are from the side surface c and the side surface d, a detection probability of first-order pileup, coordinates of first and second incident photons in the z direction, an energy of the first and second incident photons, a time interval between an arrival of the first and the second incident photons, an detector attenuation at incident energy of the first incident photon.

16. The apparatus of claim 15, wherein the processing circuitry is further configured to determine the response function for s-order pileup of s photons by summing up the calculated detector response functions for each of the subregions produced by any combination of s photons from s subregions and normalizing the summed response by a combination of the area of the top surface and the projection area of the side surfaces, where s is an integer >1.

17. The apparatus of claim 1, further comprising:
a memory that stores the overall detector response function,
wherein the processing circuitry is further configured to read out the overall detector response function from the memory and calculate the output spectrum based on the incident spectrum and the overall detector response function read out from the memory.

18. A method for calculating an output spectrum of a photon-counting detector based on an incident spectrum, the method comprising:
determining a plane extending from a top face of the photon-counting detector that includes subregions that all possible incident rays will transverse;
dividing the determined plane into subregions;
calculating a detector response function for each of the subregions;
determining an overall detector response function by summing the calculated detector response function for each of the subregions and normalizing the summation by an area of the determined plane; and
calculating the output spectrum based on the overall detector response function and the incident spectrum,
wherein the dividing step further comprises dividing the determined plane into subregions in which a first photon is located and subregions in which a second photon is located, each subregion in which the first photon is located being designated by $g_{ij}$ and each subregion in which the second photon is located being designated by $g_{kl}$, wherein i and j are indices of the subregions in which the first photon is located in X and Y dimensions, and i=0 . . . m, j=0 . . . n, k and l are indices of the subregions in which the second photon is located in the X and Y dimensions, and k=0 . . . e, l=0 . . . h, and m, n, e and h are integers.

19. A non-transitory computer-readable medium storing executable instructions, which when executed by a computer processor, cause the computer processor to execute a method comprising:
determining a plane extending from a top face of the photon-counting detector that includes subregions that all possible incident rays will transverse;
dividing the determined plane into subregions;
calculating a detector response function for each of the subregions;
determining an overall detector response function by summing the calculated detector response function for each of the subregions and normalizing the summation by an area of the determined plane; and
calculating the output spectrum based on the overall detector response function and the incident spectrum,
wherein the dividing step further comprises dividing the determined plane into subregions in which a first photon is located and subregions in which a second photon is located, each subregion in which the first photon is located being designated by $g_{ij}$ and each subregion in which the second photon is located being designated by $g_{kl}$, wherein i and j are indices of the subregions in which the first photon is located in X and Y dimensions, and i=0 . . . m, j=0 . . . n, k and l are indices of the subregions in which the second photon is located in the X and Y dimensions, and k=0 . . . e, l=0 . . . h, and m, n, e and h are integers.

* * * * *